US011779244B2

(12) United States Patent
Jaisson

(10) Patent No.: US 11,779,244 B2
(45) Date of Patent: Oct. 10, 2023

(54) DEVICE FOR MANDIBULAR ATTACHMENT OF A LOCALIZATION MARKER

(71) Applicant: MODJAW, Ste Helene du Lac (FR)

(72) Inventor: Maxime Jaisson, Les Marches (FR)

(73) Assignee: MODJAW, Ste Helene du Lac (FR)

( * ) Notice: Subject to any disclaimer, the term of this patent is extended or adjusted under 35 U.S.C. 154(b) by 1011 days.

(21) Appl. No.: 16/490,412

(22) PCT Filed: Mar. 5, 2018

(86) PCT No.: PCT/FR2018/050498
§ 371 (c)(1),
(2) Date: Aug. 30, 2019

(87) PCT Pub. No.: WO2018/158551
PCT Pub. Date: Sep. 7, 2018

(65) Prior Publication Data
US 2020/0237265 A1 Jul. 30, 2020

(30) Foreign Application Priority Data

Mar. 3, 2017 (FR) ...................................... 1751748

(51) Int. Cl.
*A61B 5/11* (2006.01)
*A61C 19/045* (2006.01)
(Continued)

(52) U.S. Cl.
CPC .......... *A61B 5/1127* (2013.01); *A61B 5/0075* (2013.01); *A61B 5/0088* (2013.01);
(Continued)

(58) Field of Classification Search
CPC ..... A61C 9/0053; A61C 19/04; A61C 19/045; A61C 2090/3912; A61C 2090/3991; A61B 5/1127
See application file for complete search history.

(56) References Cited

U.S. PATENT DOCUMENTS

| 4,432,728 A | 2/1984 | Skarky |
| 6,200,135 B1 | 3/2001 | Hultgren |

(Continued)

FOREIGN PATENT DOCUMENTS

| DE | 102014111643 A1 | 2/2016 |
| DE | 202015105356 U1 | 10/2016 |

(Continued)

OTHER PUBLICATIONS

International Preliminary Report on Patentability received for PCT Patent Application No. PCT/FR2018/050498, dated Sep. 12, 2019, 19 pages (11 pages of English Translation and 8 pages of Original Document).

(Continued)

*Primary Examiner* — Carrie R Dorna
(74) *Attorney, Agent, or Firm* — WOMBLE BOND DICKINSON (US) LLP

(57) ABSTRACT

A device for attaching a localization marker to the lower jaw of an individual. The marker includes an inner face provided with two attachment lugs including an intra-oral portion having a general U-shape adapted for coming into contact with the outer face of the teeth of the lower jaw, an extra-oral portion including an attachment element for the marker, a connecting portion connecting the intra-oral portion and the extra-oral portion. The attachment element includes two recesses each adapted for receiving a respective lug of the marker, the recesses being separated by a tab adapted for being elastically deformed when one of the lugs is engaged in a respective recess so as to exert a pressure force on the lug.

18 Claims, 4 Drawing Sheets

(51) Int. Cl.
  *A61B 90/00*    (2016.01)
  *A61B 5/00*     (2006.01)
  *A61C 19/04*    (2006.01)
(52) U.S. Cl.
  CPC .............. *A61B 5/682* (2013.01); *A61C 19/04* (2013.01); *A61C 19/045* (2013.01); *A61B 2090/397* (2016.02); *A61B 2090/3912* (2016.02); *A61B 2090/3991* (2016.02)

(56) References Cited

U.S. PATENT DOCUMENTS

| | | |
|---|---|---|
| 2005/0106529 A1 | 5/2005 | Abolfathi et al. |
| 2006/0201520 A1 | 9/2006 | Christensen, III |
| 2014/0186793 A1 | 7/2014 | Kurti et al. |
| 2016/0317108 A1 | 11/2016 | Dekel et al. |

FOREIGN PATENT DOCUMENTS

| | | |
|---|---|---|
| EP | 2499996 A1 | 9/2012 |
| WO | 2013/030511 A2 | 3/2013 |

OTHER PUBLICATIONS

International Search Report and Written Opinion received for PCT Patent Application No. PCT/FR2018/050498, dated Jun. 26, 2018, 22 pages (12 pages of English Translation and 10 pages of Original Document).

Preliminary Research Report and Written Opinion received for French Application No. 1751748, dated Oct. 23, 2017, 8 pages (1 page of French Translation Cover Sheet and 7 pages of original document).

DEVICE FOR MANDIBULAR ATTACHMENT OF A LOCALIZATION MARKER

FIELD OF THE INVENTION

The present invention relates to a device for mandibular attachment of a localization marker, notably intended to be used for recording the mandibular kinematics of an individual.

PRIOR ART

The document WO 2013/030511 describes a method for designing a dental apparatus for an individual in which the mandibular kinematics recorded on said individual are used to animate digital models of the upper and lower dental arches of the individual.

To do so, it is firstly necessary to calibrate the digital models of the arches to the planes and reference points of the individual.

Next, the mandibular kinematics of the individual are recorded. To this end, the individual is equipped with several markers:

one or more markers are positioned at the level of the forehead of the individual, through a support encircling the forehead,
one or more markers are positioned at the level of the lower jaw (mandible) and rigidly attached to the teeth of the lower arch.

A camera suitable for detecting said markers is oriented towards the face of the patient and records the displacements of the markers during movements of the mandible.

The mandibular markers may be attached directly onto the teeth of the lower arch, but this requires the use of a device for moving apart the lips to make them visible by the camera.

Another solution is to attach the marker to an intermediate support which is itself attached to the mandible. Said intermediate support must be attached in a rigid manner to the mandible, because any relative displacement with respect to the mandible during the acquisition of the mandibular kinematics would deteriorate the precision of the recording. In addition, the wearing of this intermediate support must be comfortable for the individual.

The marker is preferably supplied separately from the support, to enable firstly putting in place the support alone in the mouth of the patient, then, once the support is attached on the mandible, the marker is mounted on the support. However, if the force for putting in place the marker on the support is too high, the support may be displaced with respect to the mandible.

DESCRIPTION OF THE INVENTION

An aim of the invention is thus to design a support for a mandibular localization marker that enables a rigid attachment of the marker with respect the individual, with a system for attaching the marker that minimises the force of mounting the marker on the support.

To this end, the invention proposes a device for attaching a localization marker to the lower jaw of an individual, said marker comprising an inner face provided with two attachment lugs, comprising:

an intra-oral portion having a general U-shape suitable for coming into contact with the outer face of the teeth of the lower jaw,
an extra-oral portion comprising an element for attaching the marker,
a connecting portion connecting the intra-oral portion and the extra-oral portion,
characterised in that the attachment element comprises two recesses each suitable for receiving a respective lug of the marker, said recesses being separated by a tab suitable for being elastically deformed when one of the lugs is engaged in a respective recess so as to exert a pressure force on said lug.

According to an embodiment, the attachment element further comprises two lateral fins suitable for being deformed elastically when each lug is engaged in a respective recess so as to exert a pressure force on the inner face of the marker.

In a particularly advantageous manner, the intra-oral portion is flexible in the plane of the U.

According to a preferred embodiment, the face of the intra-oral portion oriented towards the teeth has a rough surface.

In an advantageous manner, the face of the intra-oral portion oriented towards the teeth comprises at least one notch suitable for engaging in a relief of the teeth of the lower jaw.

Preferably, the intra-oral portion is provided at its ends with divisible segments.

According to an embodiment, the attachment element comprises means for guiding and/or abutting the marker.

In a preferred manner, the attachment element is configured to enable dismantling of the marker.

In an advantageous manner, the connecting portion is designed so that, when the device is in place in the mouth of the individual, a section of said connecting portion extends substantially in the plane of the closing of the lips.

According to an embodiment, the intra-oral portion, the extra-oral portion and the connecting portion are integrally formed.

The intra-oral portion, the extra-oral portion and the connecting portion are advantageously constituted of a biocompatible material.

The invention also relates to a localization device comprising an attachment device such as described above and a marker comprising an inner face provided with two attachment lugs, said marker being attached to the extra-oral portion by engagement of each lug in a respective recess, the tab exerting a pressure force on one of the lugs.

According to an embodiment, the marker comprises a plurality of reflective patches.

The invention also relates to a localization system comprising an infrared camera and an assembly formed of the attachment device and the marker such as described previously.

Finally, the invention relates to a method for recording the mandibular kinematics of an individual by means of the localization system such as described previously, in which the marker is attached on the teeth of the mandibular arch of the individual through the attachment device, another marker provided with a plurality of reflective patches is attached on the forehead of the individual, and the relative displacements of said markers during mandibular movements made by the individual are recorded with the infrared camera.

To attach the marker on the attachment device, the inner face of the marker provided with two attachment lugs is presented facing the extra-oral portion of the device, a first lug is engaged in a first recess then a second lug in a second recess while elastically deforming the tab such that said tab exerts a pressure force on the second lug.

DESCRIPTION OF THE FIGURES

Other characteristics and advantages of the invention will become clear from the detailed description that follows, with reference to the appended drawings in which.

DETAILED DESCRIPTION OF THE INVENTION

Figure 1:
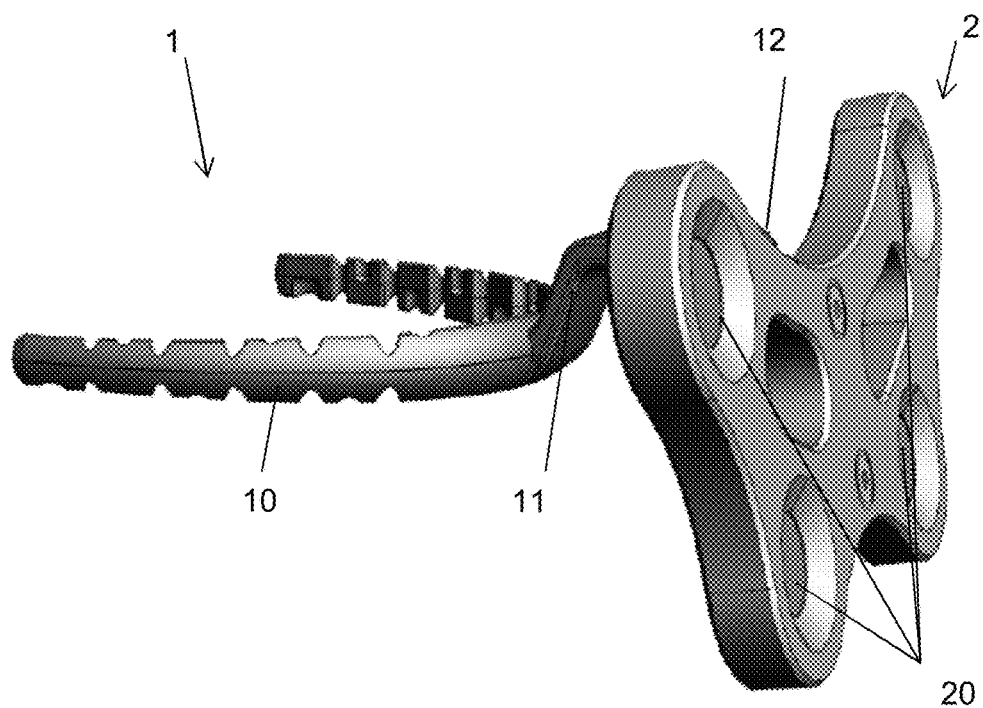
FIG. 1 is a perspective view of the mandibular attachment device equipped with a localization marker.
Figure 2:
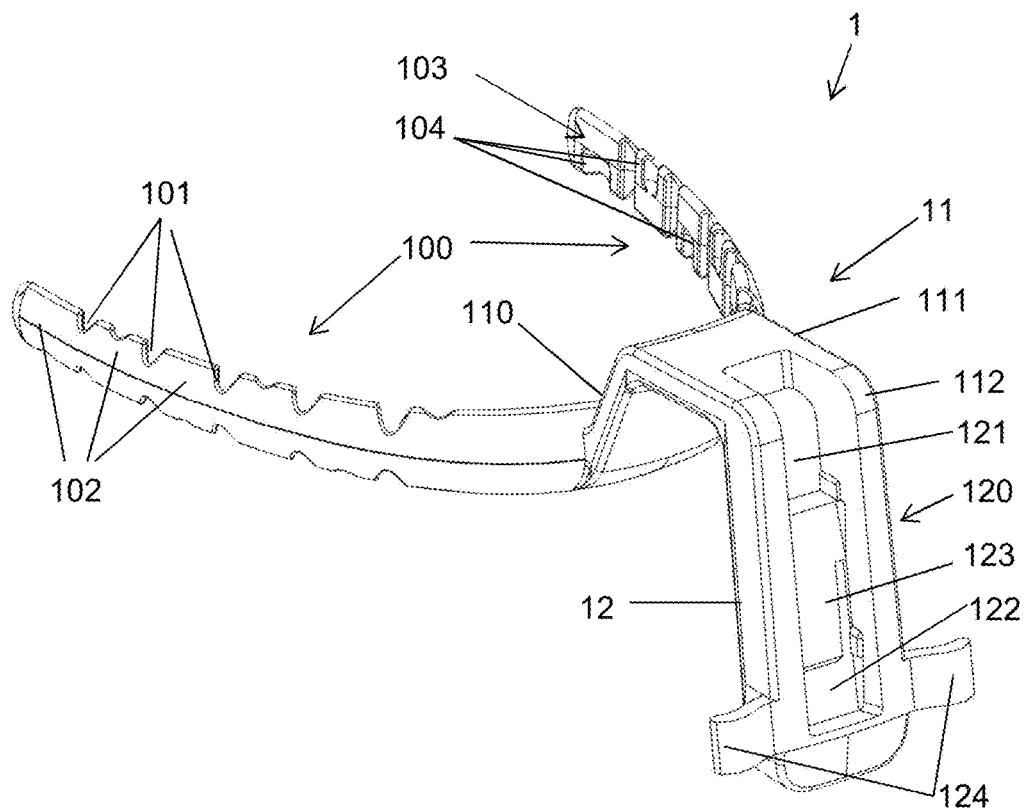
FIG. 2 is a perspective view of the mandibular attachment device of FIG. 1 in the absence of the localization marker.
Figure 3:
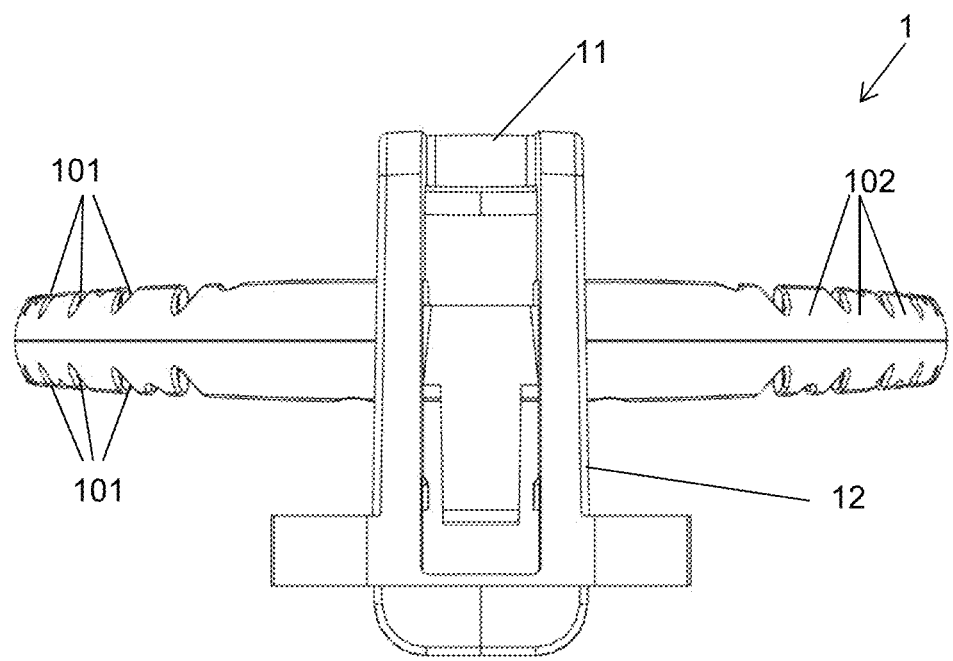
FIG. 3 is a front view of the mandibular attachment device of FIG. 2.
Figure 4:
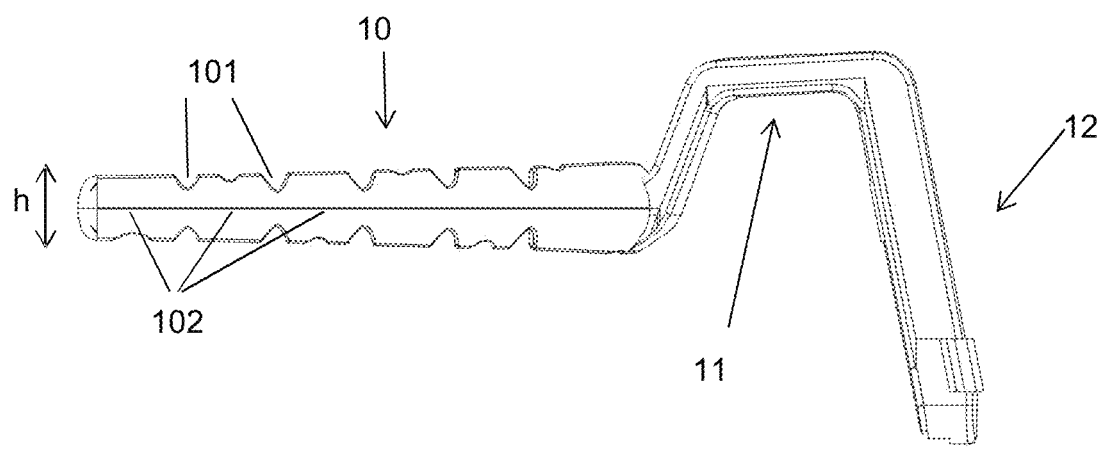
FIG. 4 is a side view of the mandibular attachment device of FIG. 2.
Figure 5:
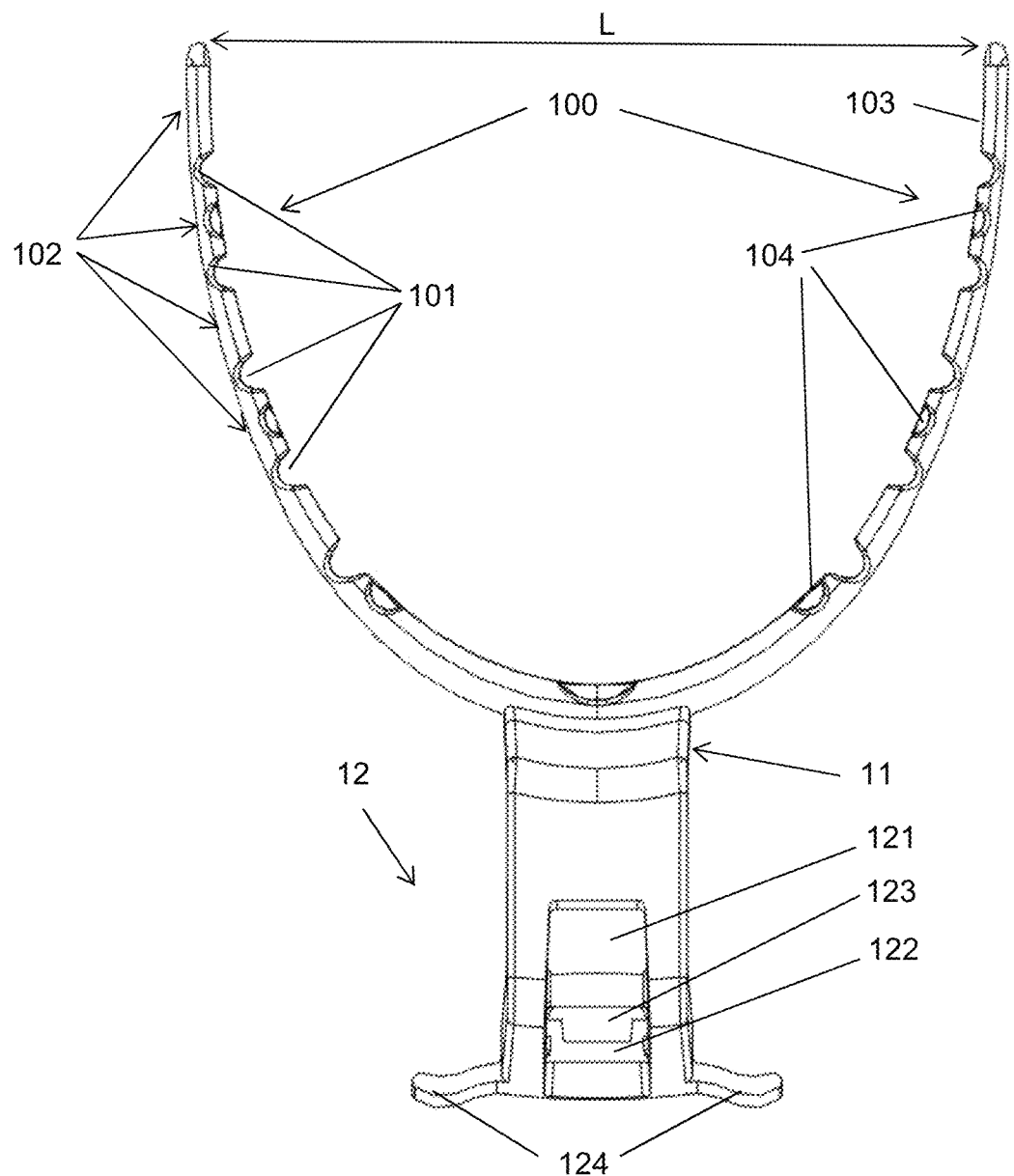
FIG. 5 is a top view of the mandibular attachment device of FIG. 2.

FIG. 1 is a perspective view of a marker 2 mounted on a mandibular attachment device 1 according to the invention.

The localization technology of the marker is not limiting.

In the example illustrated on FIG. 1, the marker comprises four reflective patches 20, the size and the relative position of which are known, detectable by an infrared camera. The shape of the patches is not limiting. Thus, said patches could be replaced by reflective elements having any other appropriate shape, for example beads.

In an alternative manner, the reflective patches could be replaced by a chart formed of a two-coloured pattern of known geometry.

According to other embodiments, the reflective patches could be replaced by diodes, electromagnetic coils, or any other appropriate localization means, such as IMUs (inertial measurement units), accelerometers, gyroscopes, etc.

As illustrated in FIG. 1, the device 1 comprises:
an intra-oral portion 10 intended to be maintained against the outer face of the teeth of the lower jaw (not represented),
an extra-oral portion 12 (more clearly visible in FIGS. 2 to 5) comprising an attachment element for the marker 2,
a connecting portion 11 making it possible to connect the intra-oral portion 10 to the extra-oral portion 12.

In a particularly advantageous manner, the whole of the three parts 10, 11, 12 is integrally formed by moulding of a biocompatible thermoplastic material.

For example, this material may be polyamide, polypropylene, PEEK (non-exhaustive list).

The device 1 is typically single-use and may thus be discarded after use.

With a view to its use, and depending on potential regulatory requirements, the mandibular attachment device may be supplied sterilised in a sealed envelope protecting it from any external contamination.

FIGS. 2 to 5 illustrate views of the mandibular attachment device without the marker.

The intra-oral portion 10 has a general U-shape.

The material and the thickness of the intra-oral portion are chosen to have a certain flexibility in a direction of moving apart or coming closer of the legs of the U in their plane.

Thus, the two legs 100 may be moved apart with respect to their initial position to be inserted in the mouth of the individual without rubbing against the teeth or the gums, then released once they have been correctly positioned.

At rest, that is to say before insertion in the mouth of the individual, the width L of the intra-oral portion is defined as being the maximum distance between the two legs of the U.

Preferably, the width of the intra-oral portion at rest is slightly less than the average width of the jaw of the individual (defined as being the distance between the outer surfaces of the molars of the lower jaw), such that once inserted into the mouth of the patient, the elasticity of the legs 100 exerts a slight compressive force on the teeth, in order to ensure the intra-oral portion is maintained correctly.

According to an optional but advantageous embodiment, the end of the legs of the U is made divisible by the presence of one or more notches 101 which define one or more detachable segments 102. Thus, one or more of said detachable segments may be removed until a length of the legs 100 is obtained adapted to the length of the jaw of the individual. The length of said segments 102 (distance between two adjacent notches 101) is typically of the order of 5 to 10 mm. The notches 101 may extend from the lower face or the upper face of the legs 100; they may also extend from two faces opposite each other, as is the case in FIGS. 1 to 5. The depth of the notches 101 (or the sum of the depths in the case of opposite notches) is typically of the order of half of the height h of each leg.

In an advantageous manner, the mechanical strength of the intra-oral portion 10 on the jaw of the patient is ensured at least in part by a biocompatible adhesive (not represented) deposited between the surface of the teeth and the inner face of the intra-oral portion. Such a biocompatible adhesive is frequently used in the dentistry field.

Furthermore, the inner face 103 of the intra-oral portion, that is to say the face intended to come into contact with the teeth, may have a certain roughness. For example, a part made by 3D printing (using the so called SLS (selective laser sintering) technique) has an appropriate roughness. In the case of a part made by moulding, the injection mould may undergo a treatment, for example a sanding or a chemical etching, conferring on it a non-smooth surface state. This roughness makes it possible to improve the mechanical strength of the adhesive vis-à-vis the inner face 103.

On the other hand, the inner face 103 of the intra-oral portion may be provided with notches 104. Said notches are arranged in such a way as to be located facing parts in relief on the outer surface of the teeth when the device is in place in the mouth of the individual. The notches 104 thus fulfil a function of blocking the intra-oral portion, notably in the anterior-posterior direction, which stabilises the device in the mouth.

In a particularly advantageous manner, the height h of the intra-oral portion is chosen sufficiently low (typically less than the average height of the teeth) in order not to go beyond the plane formed by the upper surface of the teeth of the lower jaw when the device is in place in the mouth of the individual. For example, the height h is of the order to 5 mm.

Thus, the intra-oral portion does not interfere with the mandibular kinematics (clenching of the teeth, chewing movements and others).

The extra-oral portion 12 has for its part an attachment element 120 for a marker.

Figure 6:
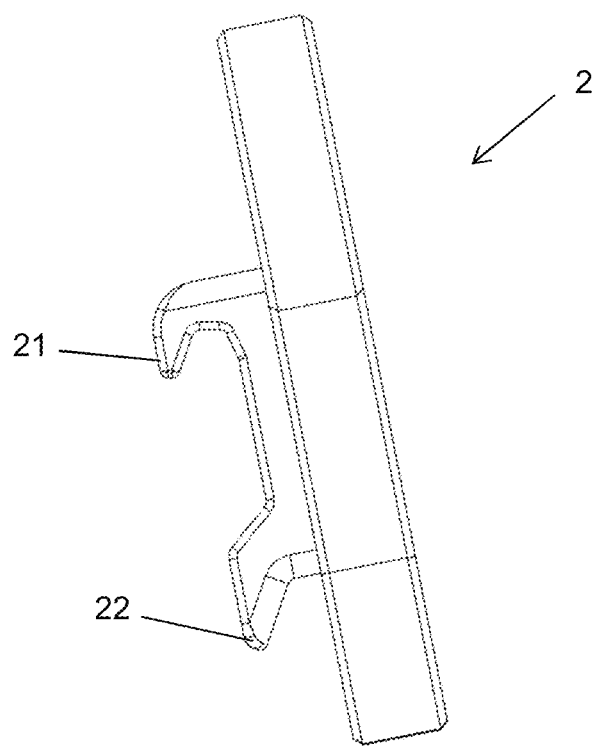
FIG. 6 is a side view of the mandibular marker.

In the example illustrated in the appended figures, the marker 2 is attached by snap coupling on the extra-oral portion 12. To this end, as illustrated in FIG. 6, the mandibular marker 2 comprises, on its inner face (i.e. opposite to the reflective patches), two lugs 21, 22 arranged one above the other (considering the position of the marker when it is in place on the individual). The attachment element 120 comprises two recesses 121, 122 separated by an elastic tab 123. To put in place the marker 2 on the attachment device 1, the upper lug 21 is firstly engaged in the recess 121, then the lower lug is engaged in the recess 122, this engagement causing a slight deformation of the tab 123 rearwards (that is to say on the side opposite the reflective patches). The marker is thus maintained on the extra-oral portion 12 by engagement of the lugs 21, 22 in the recesses 121, 122 and by a pressure force exerted by the deformed tab 123.

The assembly of the marker 2 on the attachment device is advantageously carried out once the attachment device has been put in place in the mouth of the patient and attached using the aforesaid biocompatible adhesive. Thus, the marker does not hinder this putting in place operation.

Thanks to the attachment mechanism described above, the marker can be manipulated with a single hand by the practitioner to be put in place on the extra-oral portion of the device.

Furthermore, the force required to put in place the marker on the extra-oral portion is very low, such that it does not affect the mechanical strength of the attachment device vis-à-vis the mandible.

In a particularly advantageous manner, the attachment element 120 further comprises two lateral elastic fins 124, which are deformed during the putting in place of the mandibular marker on the extra-oral portion 12. Said fins then exert a pressure force on the inner face of the marker, which further stabilises its attachment.

It will be noted that the putting in place of the marker is particularly facilitated when the lugs and recesses are arranged one above the other in the use position of the device, because the upper recess is easily accessible to the practitioner. However, a similar architecture with an alignment of the recesses and the tab in a horizontal plane, or according to any inclination, could also be implemented without however going beyond the scope of the present invention. For example, the extra-oral portion could comprise a right recess and a left recess aligned in a horizontal plane and, for the assembly, the marker should be presented in front of the extra-oral portion with the lugs aligned along a horizontal plane, in order to enable the engagement of the lugs in the recesses and the deformation of the tab in a horizontal plane.

The extra-oral portion is designed to be sufficiently rigid to support the weight of said marker without being deformed.

Preferably, the mode for attaching the marker 2 on the extra-oral portion 12 is chosen so as not to require any tool. For example, the extra-oral portion may have an element enabling the snap connection of the marker, a quarter turn type attachment, or even a magnetic force, etc. In the latter case, the extra-oral portion and the marker are respectively provided with a magnet and/or an element made of ferrous material intended to cooperate with the magnet.

In a particularly advantageous manner, the marker can be detached from the attachment device.

According to an embodiment, the attachment for the marker is moreover reproducible, that is to say that each time that the marker is put in place on the device, the position of the marker with respect to the device is identical.

To this end, the attachment element 120 provided on the extra-oral portion 12 comprises means for guiding and/or abutting the marker.

According to a less preferred embodiment, the marker could form an integral part of the extra-oral portion.

When the device 1 is in place in the mouth of the individual, the extra-oral portion 12 is advantageously situated below the plane of the lips of the individual (the marker 20 being able for its part to go beyond this plane).

For reasons of stability of the device, said device is substantially symmetrical with respect to the anterior-posterior plane of the individual.

The connecting portion 11 between the intra-oral 10 and extra-oral 12 portions is like a bridge clamp extending from the central region of the intra-oral portion 10. This bridge clamp has a first section 110 extending towards the upper jaw, a second section 111 extending through the lips and a third section 112 for connecting to the extra-oral portion 12.

The shape and the dimensions of the connecting portion are chosen so that, when the device is in place in the mouth of the individual, the second section 111 extends to the level of the plane of the lips, without exerting pressure on the lips. The device 1 remains immobile even in the event of swallowing.

Furthermore, the connecting portion 11 is designed to be sufficiently rigid so as not to deform when the marker 20 is attached to the extra-oral portion 12.

The device 1 and the marker 2 form part of a localization system in which they are associated with a camera, notably an infrared camera in the case of a marker provided with reflective patches.

To record the mandibular kinematics of an individual, the intra-oral portion is attached in contact with the teeth of the lower arch of the individual, then the marker is attached to the extra-oral portion.

The individual is also equipped with a forehead support also bearing a localization marker according to the same technology as the mandibular marker. Optionally, it is possible to do without such a forehead support by equipping the upper jaw with an attachment device similar to that which has just been described, with shapes and dimensions adapted to this jaw.

The putting in place of these markers on the individual is naturally carried out in a non-invasive manner.

The camera is placed opposite the patient, such that the forehead marker and the mandibular marker are permanently within his field of vision.

The individual then carries out a certain number of mandibular movements (chewing, etc.) according to the recommendations of the practitioner.

The camera detects and records the relative displacements of the markers.

After the acquisition, this recording is applied to digital models of the dental arches of the individual, which makes it possible to animate them.

The invention claimed is:

1. A localization device, comprising:
   a localization marker comprising an inner face provided with two attachment lugs, and
   a device for attaching the localization marker to a lower jaw of an individual, comprising:
   an intra-oral portion having a general U shape adapted for coming into contact with an outer face of teeth of the lower jaw,
   an extra-oral portion comprising an attachment for the marker, and
   a connecting portion connecting the intra-oral portion and the extra-oral portion,
   wherein the attachment comprises two recesses each adapted for receiving a respective lug of the localization marker, said recesses being separated by a tab adapted for being elastically deformed when one of the lugs is engaged in a respective recess so as to exert a pressure force on said lug, the localization marker being attached to the extra-oral portion by engagement of each lug in a respective recess, the tab exerting a pressure force on one of the lugs, and the localization marker comprising a plurality of reflective patches or beads.

2. A localization system comprising an infrared camera and the localization device of claim 1, the infrared camera being configured to detect the plurality of reflective patches of the localization marker.

3. A method for recording a mandibular kinematics of an individual by means of the localization device of claim 1 and an infrared camera configured to detect the plurality of reflective patches of the localization marker, wherein the localization marker is attached on the teeth of the mandibular arch of the individual through the attachment device, another marker provided with a plurality of reflective patches is attached on the forehead of the individual, and relative displacements of said markers during mandibular movements made by the individual are recorded with the infrared camera.

4. The method of claim 3, wherein, to attach the localization marker on the attachment device, the inner face of the localization marker provided with the two attachment lugs is presented facing the extra-oral portion of the device, a first lug is engaged in a first recess then a second lug is engaged in a second recess while elastically deforming the tab such that said tab exerts a pressure force on the second lug.

5. The localization device of claim 1, wherein the attachment further comprises two lateral fins adapted for deforming elastically when each lug is engaged in a respective recess so as to exert a pressure force on the inner face of the marker.

6. The localization device of claim 1, wherein the intra-oral portion is flexible in the plane of the U.

7. The localization device of claim 1, wherein the face of the intra-oral portion oriented towards the teeth has a rough surface.

8. The localization device of claim 1, wherein the face of the intra-oral portion oriented towards the teeth comprises at least one notch adapted for engaging in a relief of the teeth of the lower jaw.

9. The localization device of claim 1, wherein the intra-oral portion is provided at its ends with divisible segments.

10. The localization device of claim 1, wherein the attachment comprises at least one of a guide and an abutment for the localization marker.

11. The localization device of claim 1, wherein the attachment is configured to enable dismantling of the localization marker.

12. The localization device of claim 1, wherein a shape and dimensions of the connecting portion are chosen so that, when the device is in place in the mouth of the individual, a section of said connecting portion extends substantially in the plane of the closing of the lips.

13. The localization device of claim 1, wherein the intra-oral portion, the extra-oral portion and the connecting portion are integrally formed.

14. The localization device of claim 1, wherein the intra-oral portion, the extra-oral portion and the connecting portion comprise a biocompatible material.

15. The localization device of claim 1, wherein the intra-oral portion presents a height selected such that the intra-oral portion does not extend beyond a plane formed by an upper surface of the teeth of the lower jaw when the device is in place in the individual's mouth.

16. The localization device of claim 1, wherein the device is configured such that when the device is in place in the individual's mouth, the extra-oral portion is situated below a plane of the individual's lips.

17. The localization device of claim 1, wherein the device is substantially symmetrical with respect to an anterior-posterior plane of the individual.

18. A localization device, comprising:
a localization marker comprising an inner face provided with two attachment lugs, and
a device for attaching the localization marker to a lower jaw of an individual, comprising:
an intra-oral portion having a general U shape adapted for coming into contact with an outer face of teeth of the lower jaw,
an extra-oral portion comprising an attachment for the marker, and
a connecting portion connecting the intra-oral portion and the extra-oral portion,
wherein the attachment comprises two recesses each adapted for receiving a respective lug of the localization marker, said recesses being separated by a tab adapted for being elastically deformed when one of the lugs is engaged in a respective recess so as to exert a pressure force on said lug,
the localization marker being attached to the extra-oral portion by engagement of each lug in a respective recess, the tab exerting a pressure force on one of the lugs, and
the localization marker comprising at least one of: a chart formed of a two-coloured pattern of known geometry, a diode, an electromagnetic coil, an inertial measurement unit, an accelerometer and a gyroscope.

* * * * *